US008416963B2

(12) United States Patent
Park et al.

(10) Patent No.: US 8,416,963 B2
(45) Date of Patent: Apr. 9, 2013

(54) SYSTEM FOR PROVIDING A PERSONALIZED DRIVING SOUND

(75) Inventors: Dong Chul Park, Gyeonggi-do (KR); Sang Young Park, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 276 days.

(21) Appl. No.: 12/625,332

(22) Filed: Nov. 24, 2009

(65) Prior Publication Data

US 2010/0329477 A1 Dec. 30, 2010

(30) Foreign Application Priority Data

Jun. 25, 2009 (KR) ........................ 10-2009-0056969

(51) Int. Cl.

| | |
|---|---|
| ***H04B 1/00*** | (2006.01) |
| ***H03G 3/00*** | (2006.01) |
| ***A61F 11/06*** | (2006.01) |
| ***G10K 11/16*** | (2006.01) |
| ***H03B 29/00*** | (2006.01) |

(52) U.S. Cl. ............................ 381/86; 381/61; 381/71.4

(58) Field of Classification Search .................... 381/86, 381/61, 71.4, 73.1, 56, 63, 62, 77, 334; 446/7
See application file for complete search history.

(56) References Cited

U.S. PATENT DOCUMENTS

2004/0170288 A1 9/2004 Maeda
2006/0074645 A1* 4/2006 Tischer ......................... 704/226
2009/0287545 A1* 11/2009 Albright ......................... 705/10

FOREIGN PATENT DOCUMENTS

JP 04-160900 A 6/1992
JP 05-024482 A 2/1993
JP 07-032948 A 2/1995
JP 07-182587 A 7/1995
JP 2003-276504 A 10/2003
JP 2004-061200 A 2/2004
JP 2008-273228 A 11/2008

* cited by examiner

*Primary Examiner* — Xu Mei
*Assistant Examiner* — Douglas Suthers
(74) *Attorney, Agent, or Firm* — Edwards Wildman Palmer LLP; Peter F. Corless

(57) ABSTRACT

The present invention relates to a system for providing a personalized driving sound by using an active sound design. The system includes a sound design tool, a memory card, and an audio system. The sound design tool enables a user to create the driving sound. The memory card receives and stores the created driving sound from the sound design tool. The audio system outputs the driving sound stored in the memory card.

12 Claims, 3 Drawing Sheets

SYSTEM FOR PROVIDING A PERSONALIZED DRIVING SOUND

CROSS-REFERENCE TO RELATED APPLICATION

This application claims under 35 U.S.C. §119(a) the benefit of Korean Patent Application No. 10-2009-0056969 filed on Jun. 25, 2009, the entire contents of which are incorporated herein by reference.

BACKGROUND OF THE INVENTION

Active noise control (ANC) is a technique for reducing vehicle noise, and controls the noise of booming bandwidth having a frequency of 250 Hz or less by using an inverted phase sound wave to the noise. When a noise is generated, active noise control emits a sound wave having an inverted phase to the original noise through an audio apparatus, thereby canceling the noise.

In general, noise control methods can largely be divided into methods that can reduce noise emission from a noise source, methods that can block noise by using sound absorbing material, and methods that can cancel noise by using active noise control. Among these methods, the method of using sound absorbing material is effective with respect to a high frequency noise higher than 500 Hz. However, in the case of a low frequency noise, the size of the sound absorbing material needs to be suitably increased, which results in increased cost. Accordingly, when weight reduction is desirable, such as for an aircraft or a vehicle, the method may not be suitable.

Research has been conducted on active noise control that uses a secondary source, and it has been found that active noise control shows an excellent effect compared to conventional manual methods in canceling a low frequency noise, for example, a noise generated in a rotary machine, a transformer, or a car engine.

Research studies have been developed concerning noise control in a duct, an active noise control in three-dimensional space such as a plant or an office, the design of a noise barrier using the active noise control, and an active noise control in a vehicle or an airplane. More recently, due to increasing environmental awareness, there has been an increasing demand for a car that consumes less fuel so as to reduce the emission of exhaust gases. Accordingly, research has been initiated directed to reducing the weight of a car while, at the same time, increasing engine efficiency. However, so far, this approach has resulted in increased noise and vibration in the car.

At the same time, there is a demand from customers for more comfortable and quiet cars, and active noise control has been proposed as a solution to such demand due to its ability to actively control the interior noise of a car.

A noise generated in a car interior, which is an enclosed space, can include engine noise, road noise that depends on the structure of the surface layer of road pavement, or wind noise around doors and windows that is produced during driving. Among these noises, the engine noise, which has a strong correlation with frequency of rotation, occupies a considerable portion of the entire interior noise of car.

In a typical active noise control system for controlling vehicle interior noise, for example as illustrated in FIG. 1, the vehicle interior noise sensed by a microphone 1 is suitably filtered through a filter 2 and is inputted to a controller 5 through an analog-to-digital (A/D) converter 3. Preferably. the controller 5 applies multiple algorithms to the input value to produce a computed result by which the current level of the noise can be adjusted to be minimized. Based on the computed result, a control signal is digital-to-analog converted by using a D/A converter and then is provided to an amplifier 4. Preferably. the control signal, of which level is amplified by the amplifier 4, is outputted through a speaker 6.

In the above-described active noise control apparatus for a vehicle, a noise reduction function is utilized to minimize a car noise in order to reduce an engine booming sound. However, there is also a need to cancel noises other than a noise at a specific RPM range.

The above information disclosed in this the Background section is only for enhancement of understanding of the background of the invention and therefore it may contain information that does not form the prior art that is already known in this country to a person of ordinary skill in the art.

SUMMARY OF THE INVENTION

The present invention provides a system for providing a personalized driving sound by using an active sound design, the system preferably comprising: a sound design tool suitably configured to enable a user to create the driving sound; a memory card suitably configured to receive and store the created driving sound from the sound design tool; and an audio system suitably configured to output the driving sound stored in the memory card.

Preferably, the system provides an environment where the user can produce a user-desired driving sound by using the sound design tool. In preferred embodiments, the driving sound further includes a quiet sound and a dynamic sound. In other preferred embodiments, the driving sound can be uploaded online, and the memory card can download and store a wanted driving sound online. Preferably, the system further comprises an online customer relation management system. In certain preferred embodiments, the memory card is a mozen Bluetooth memory card. In other preferred embodiments of the present invention, the system further comprises a microphone, a control unit, a selector, and a speaker. Preferably, the control unit is built in the audio system. In preferred embodiments, the audio system includes a remote control for selecting the driving sound. Preferably, the selector includes a mood detection system.

It is understood that the term “vehicle” or “vehicular” or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum).

As referred to herein, a hybrid vehicle is a vehicle that has two or more sources of power, for example both gasoline-powered and electric-powered.

The above features and advantages of the present invention will be apparent from or are set forth in more detail in the accompanying drawings, which are incorporated in and form a part of this specification, and the following Detailed Description, which together serve to explain by way of example the principles of the present invention.

The above features and advantages of the present invention will be apparent from or are set forth in more detail in the accompanying drawings, which are incorporated in and form a part of this specification, and the following Detailed Description, which together serve to explain by way of example the principles of the present invention.

BRIEF DESCRIPTION OF THE DRAWINGS

The above and other features of the present invention will now be described in detail with reference to certain exemplary embodiments thereof illustrated by the accompanying drawings which are given hereinafter by way of illustration only, and thus are not imitative of the present invention, and wherein.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

DETAILED DESCRIPTION OF THE EMBODIMENTS

As described herein, the present invention includes a system for providing a personalized driving sound by using an active sound design, the system comprising a sound design tool, a memory card, and an audio system.

In one embodiment, the sound design tool is configured to enable a user to create the driving sound.

In another embodiment, the memory card is configured to receive and store the driving sound from the sound design tool.

In another embodiment, the audio system is configured to output the driving sound stored in the memory card.

The invention also features motor vehicles comprising the system of any one the aspects above.

Figure 1:
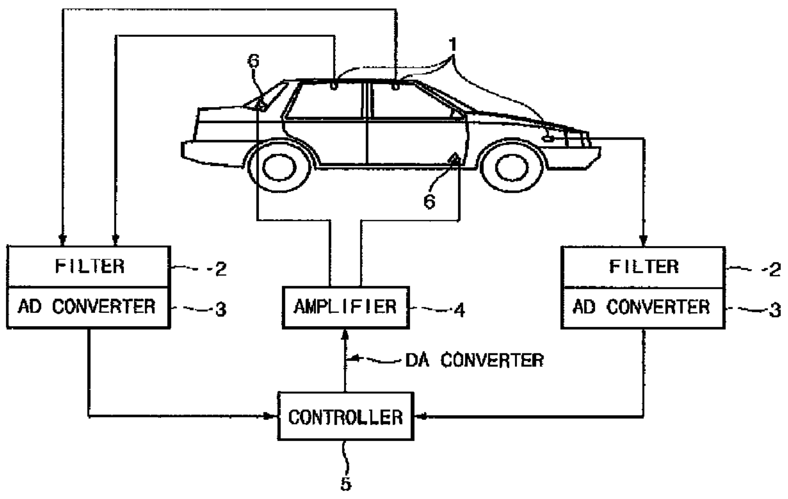
FIG. 1 is an exemplary configuration diagram showing a general active noise control system.
Figure 2:
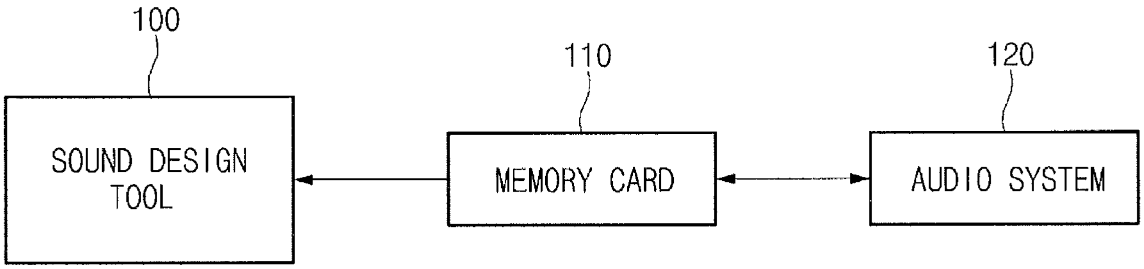
FIG. 2 is a schematic block diagram illustrating a system for providing a personalized driving sound according to preferred embodiments of the present invention.

Hereinafter, exemplary embodiments of the present invention will be described in detail with reference to the attached drawings According to certain preferred embodiments of the invention, for example as shown in FIG. 2, FIG. 2 is a schematic block diagram illustrating a system for providing a personalized driving sound according to the present invention. Preferably, the system for providing the personalized driving sound includes a sound design tool 100, a memory card 110, and an audio system 120.

In a particular preferred embodiment, for example referring to FIG. 2, the sound design tool 100 is an apparatus for producing a personalized driving sound and is capable of producing data based on various types of sounds or driving sounds.

Preferably, the driving sounds of various kinds produced in the sound design tool 100 are uploaded on a vehicle sound sale network. In further preferred embodiments, the vehicle sound sale network can be suitably implemented online and can use a customer relation management system.

In another preferred embodiment, the driving sound is stored in the memory card 110 and is suitably mounted on the audio system 120. Preferably, the stored driving sound can be classified into quiet sounds or dynamic sounds, and it is possible for users to create the driving sound of their own by using the sound design tool 100. In certain exemplary embodiments, a Mozen or a Bluetooth can be used instead of the memory card to receive and store the driving sound.

Figure 3:
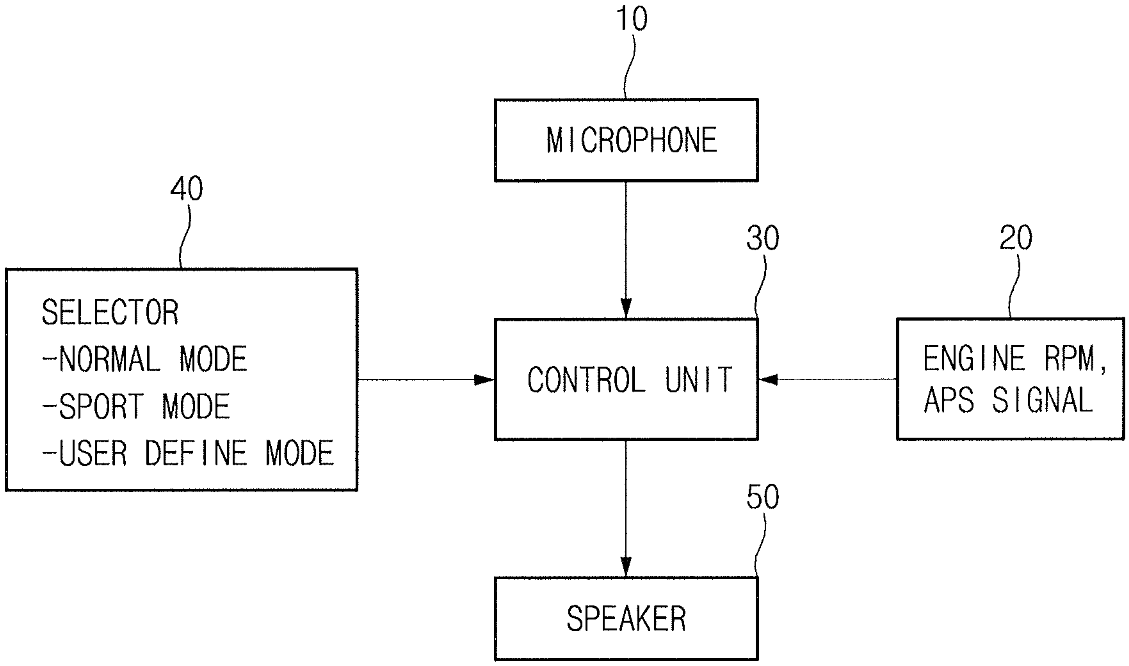
FIG. 3 is a configuration diagram illustrating a system for an active sound design (ASD) according to preferred embodiments of the present invention.

In particular preferred embodiments, for example as shown in FIG. 3, FIG. 3 is a configuration diagram illustrating a system for active sound design (ASD) according to the present invention. Preferably, the system includes a microphone 10, an engine RPM and an APS signal 20, a control unit 30, a selector 40 and a speaker 50.

Preferably, with reference to FIG. 3, the system includes the microphone 10 for suitably sensing a noise, the control unit 30 for suitably sensing the engine RPM and the APS signal 20 based on the noise sensed by the microphone 10 to embody a predefined target acceleration sound or driving sound for an entire RPM range, the selector 40 for suitably selecting the acceleration sound or the driving sound, and the speaker 40 for suitably outputting the acceleration sound or the driving sound under the control of the control unit 30.

In other preferred embodiment, the present invention utilizes a customer community that is based on the active sound design (ASD) while allowing customers to produce and share various kinds of driving sounds of their own through online. Preferably, in addition, the present invention allows customers to select a mode for a driving sound such as, but not limited only to, a quiet sound, a dynamic sound, or a user-defined driving sound, thereby providing a business model of providing a personalized driving sound.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A system for providing a personalized driving sound by using an active sound design, the system comprising:

a sound design tool configured to enable a user to create the driving sound uploaded on a vehicle sound sale network wherein the sound design tool is configured to enable a user to create a personalized driving sound on the vehicle sales network that is then downloaded to a vehicle;

a memory card configured to receive and store the driving sound from the sound design tool; and an audio system configured to output one or more user created driving sounds stored in the memory card.

2. The system of claim 1, wherein the driving sound further includes a quiet sound and a dynamic sound.

3. The system of claim 1, wherein the driving sound can be uploaded online, and the memory card can download and store a desired driving sound online.

4. The system of claim 3, further comprising an online customer relation management system.

5. The system of claim 1, wherein the memory card is used by a mozen or a Bluetooth to receive and store the one or more driving sound.

6. The system of claim 1, further comprising a microphone, a control unit, a selector, and a speaker.

7. The system of claim 6, wherein the control unit is built in the audio system.

8. The system of claim 7, wherein the audio system includes a remote control for selecting the driving sound.

9. The system of claim 1, wherein the selector includes a mood detection system.

10. A system for providing a personalized driving sound by using an active sound design, the system comprising:

a sound design tool configured to receive and upload driving sounds on a vehicle sale network by a user wherein the sound design tool is configured to enable a user to create a personalized driving sound on the vehicle sales network that is downloadable to a vehicle;

a memory card storing one or more driving sounds that have been uploaded to the sound design tool; and an audio system outputting the one or more user created driving sounds downloaded from the vehicle sale network from the memory card.

11. A motor vehicle comprising the system of claim 1.

12. A motor vehicle comprising the system of claim 10.

* * * * *